United States Patent [19]

Marciel

[11] Patent Number: Plant 7,559

[45] Date of Patent: Jun. 18, 1991

[54] MINIATURE ROSE NAMED DEVRICO

[75] Inventor: Stanley G. Marciel, Aptos, Calif.

[73] Assignee: DeVor Nurseries, Inc., Watsonville, Calif.

[21] Appl. No.: 506,222

[22] Filed: Apr. 9, 1990

[51] Int. Cl.[5] ..... A01H 5/00

[52] U.S. Cl. ..... Plt./10

[58] Field of Search ..... Plt./7, 10, 1, 6

*Primary Examiner*—Howard J. Locker

*Attorney, Agent, or Firm*—Charles W. Rummler

[57] ABSTRACT

A new and distinct miniature rose plant adapted for 4 in. pot culture and particularly distinguished by its profuse production of dark red flowers on a small, compact bush having a height of about 17 cm. when grown for six weeks in a 4 in. pot; and having abundant foliage and a vigorous, upright growth habit.

1 Drawing Sheet

BACKGROUND OF THE NEW PLANT

This new miniature rose plant originated as a seedling of a hybrid produced by me at my nursery at Watsonville, Calif., and resulting from my crossing of the variety 'Candia' with pollen from an unknown seedling selected from nursery plants maintained for breeding purposes, the objective of this crossing being to produce a well-balanced, profusely blooming variety for growing in a 4 in. pot. The present variety appearing to meet my objectives, was propagated by me by means of cuttings at Watsonville with very satisfactory results and such propagation was continued under my direction through several successive generations which demonstrated conclusively that the novel characteristics of my selected seedling would hold true from generation to generation and appeared to be firmly fixed.

DESCRIPTION OF THE DRAWING

My new rose plant is illustrated by the accompanying photographic drawings of which

DESCRIPTION OF THE NEW VARIETY

Figure 1:
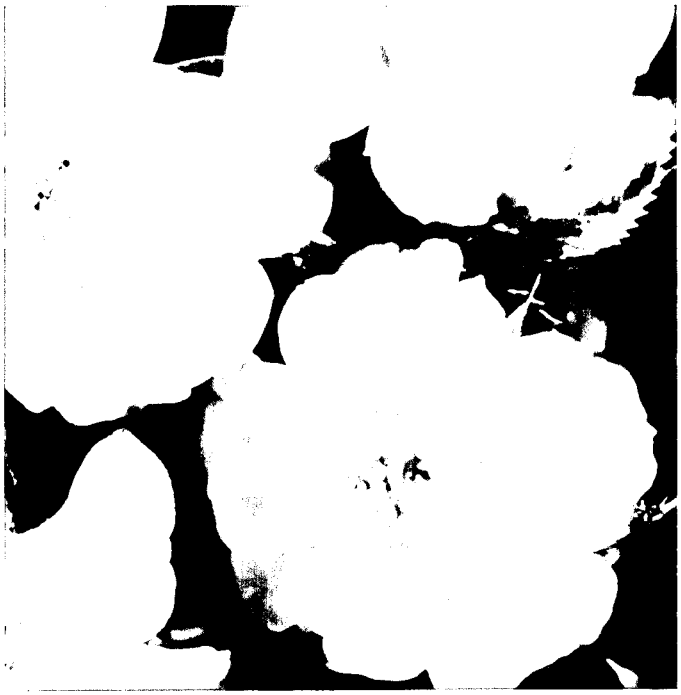
FIG. 1 shows a face view of one bloom and portions of others to illustrate the flower form and color.
Figure 2:
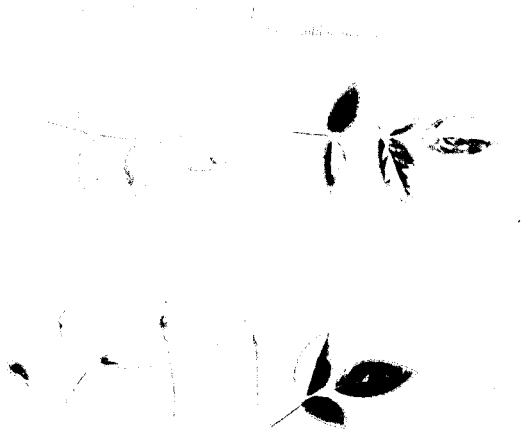
FIG. 2 shows upper and under sides of a typical leaf together with buds in several stages of development and a face view of a single flower; the colors shown being as nearly true to those herein specified as is reasonably possible to obtain by conventional photographic procedures.

The following is a detailed description of my new miniature rose plant based upon observation of plants grown in greenhouse at Watsonville with color designations specified according to the R.H.S. Colour Chart published by The Royal Horticultural Society of London, England.

THE PLANT

Origin: Seedling.

Parentage.

*Seed parent.*—The variety 'Candia' (unpatented).

*Pollen parent.*—An unknown seedling.

Classification:

*Botanic.*—Hybrid miniature rose.

*Commercial.*—Miniature pot rose.

Form: Small, compact bush.

Height: About 17 to 18 cm. at the age of six weeks in a 4 in. pot.

Growth habit: Vigorous, sturdy and upright.

Cane:

*Length.*—About 118 to 138 mm. from last flower cut.

*Color.*—Yellow, 146-B.

Branching character: Free branching.

Strength: Sturdy for a mini-flora bush.

Foliage:

*Quantity.*—Abundant.

Number of leaves.—5 or 6 from last flower cut.

*Size of leaves*—About 66 mm. long.

*Leaflets.*—Size: About 31 mm. long and 17 mm. wide. Shape: Ovate with denticulate margin. Texture: Leathery and smooth. Aspect: Glossy. Color: Upper side — Green 137-A. Under side — Yellow 147-B.

*Rachis.*—45 to 50 mm. long on 5 part leaf; and about 34 to 40 mm. long on 3 part leaf.

*Petioles.*—About 8 to 12 mm. long.

Ribs and veins: Depressed on upper side and rounded on lower side.

Thorns: Declining.

*Size.*—About 5 mm.

*Color.*—Greyed Red 181-B.

THE BUD size: Small.

*Diameter.*—About 9 mm.

*Length.*—About 11 mm.

Shape: Slender and pointed.

Rate of opening: Slow.

Color of petals:

*When sepals first divide.*—Red 45-A.

*When petals begin to unfurl.*—Red 45-A.

Sepals:

*Number.*—Five.

*Shape.*—Spreading with small, protruding leafs.

*Character.*—The sepals are hooded over the bud before dividing and curl back when the flower opens.

*Color.*—Inside — Yellow Green 147-B, with a covering of white hairs. Outside — Yellow Green 144-A.

Calyx:

*Shape.*—Funnel shaped.

*Width.*—About 5 mm.

*Length.*—About 4 mm.
*Size.*—Small.
*Splitting.*—Calyx does not split.
*Aspect.*—Smooth.

Flower stem:
*Length.*—About 29 to 37 mm.
*Character.*—Erect and slender.
*Color.*—Yellow Green 144-A.

THE FLOWER

Blooming habit: Continuous and profusely from early Spring through mid-season to late Fall; blooming freely year round under greenhouse conditions.

Size of bloom: Medium.
*Diameter.*—About 34 mm.
*Depth.*—About 10 mm.

Borne: Singly.

Form:
*When bloom first opens.*—high center.
*When bloom matures.*—slightly flattened.

Petalage:
i Number.—12 or more.
*Arrangement.*—Imbricated.
*Form.*—Oval.
*Texture*—Soft.
*Appearance.*—Velvety.
*Color.*—Red 45-A with base of Yellow 3-C. Reverse side — Red 42-A.

Petaloids:
*Number.*—3 or 4.
*Size.*—About 7 mm.
*Color.*—Red 45-A.

Fragrance: Slight.

Persistence: The flower hangs on and dries.

Discoloration after full bloom: Fades from 45-A to 44-A.

Disease resistance: Moderately resistant to mildew, rust, and black spots as observed at Watsonville, Calif.

Lasting quality: Long lasting on the plant and moderate as a cut flower.

THE REPRODUCTIVE ORGANS

Stamens:
*Number.*—About 61 to 65.
*Arrangement.*—Slightly antrorse.
*Anthers.*—Size: About 2 mm. Color: Yellow Orange 18-A.
*Filaments.*—Length: About 4 mm.
*Color: Yellow* 10-B.
*Pollen.*—Color: Yellow Orange 18-A.

Pistils:
*Number.*—about 29.
*Styles.*—Length: About 9 mm. Color: Yellow 4 -D becoming Red 51-C near the top.
*Stigmas.*—Color: Yellow 8-C.

Character of the ovaries: Oval, slightly flattened and covered with silvery hairs.

I claim:

1. The new and distinct miniature rose variety substantially as herein shown and described, characterized by its profuse and continuous production of medium sized blooms on a small, compact bush having a height of about 17 cm. when grown on a 4 in. pot; the plant being free branching and having a vigorous, upright growth habit.

* * * * *